(12) United States Patent
Hviid et al.

(10) Patent No.: US 10,405,081 B2
(45) Date of Patent: Sep. 3, 2019

(54) INTELLIGENT WIRELESS HEADSET SYSTEM

(71) Applicant: BRAGI GmbH, München (DE)

(72) Inventors: Nikolaj Hviid, München (DE); Alex Pohl, München (DE); Mohamed Ali Razouane, München (DE)

(73) Assignee: BRAGI GmbH, München (DE)

( * ) Notice: Subject to any disclaimer, the term of this patent is extended or adjusted under 35 U.S.C. 154(b) by 0 days.

(21) Appl. No.: 15/874,594

(22) Filed: Jan. 18, 2018

(65) Prior Publication Data

US 2018/0227658 A1 Aug. 9, 2018

Related U.S. Application Data

(60) Provisional application No. 62/456,548, filed on Feb. 8, 2017.

(51) Int. Cl.
*H04R 1/10* (2006.01)
*A61B 5/117* (2016.01)
(Continued)

(52) U.S. Cl.
CPC ............ *H04R 1/1041* (2013.01); *A61B 5/117* (2013.01); *G06F 3/017* (2013.01); *G06F 3/165* (2013.01);
(Continued)

(58) Field of Classification Search
None
See application file for complete search history.

(56) References Cited

U.S. PATENT DOCUMENTS

| 2,325,590 A | 8/1943 | Carlisle et al. |
| 2,430,229 A | 11/1947 | Kelsey |

(Continued)

FOREIGN PATENT DOCUMENTS

| CN | 204244472 U | 4/2015 |
| CN | 104683519 A | 6/2015 |

(Continued)

OTHER PUBLICATIONS

The Dash—A Word From Our Software, Mechanical and Acoustics Team + An Update (Mar. 11, 2014).

(Continued)

*Primary Examiner* — Tan X Dinh
(74) *Attorney, Agent, or Firm* — Goodhue, Coleman & Owens, P.C.

(57) ABSTRACT

An intelligent wireless headset system in embodiments of the present invention may have one or more of the following features: (a) a left ear portion having at least one microphone and at least one speaker associated therewith, (b) a right ear portion having at least one microphone and at least one speaker associated therewith, (c) a connecting band between the left ear portion and the right ear portion, (d) a wireless radio transceiver disposed within the intelligent wireless headset, (e) a cellular transceiver disposed within the intelligent wireless headset, (f) a headset network capable of operably coupling the intelligent wireless headset with at least one device in the headset network, (g) sensors to collect biometric information, (h) a camera for collecting video information, (i) outer speakers located on the housing, and (j) a memory for storing biometric information.

8 Claims, 5 Drawing Sheets

(51) Int. Cl.
　　　G06F 3/16　　　　(2006.01)
　　　G06F 3/01　　　　(2006.01)
　　　H04N 5/225　　　(2006.01)
　　　H04M 1/60　　　　(2006.01)

(52) U.S. Cl.
　　　CPC ........ H04M 1/6066 (2013.01); H04N 5/2253
　　　　　　(2013.01); H04N 5/2257 (2013.01); H04R
　　　　　　1/1083 (2013.01); H04R 1/105 (2013.01);
　　　　　　H04R 1/1008 (2013.01); H04R 2201/107
　　　　　　(2013.01); H04R 2420/07 (2013.01); H04R
　　　　　　　　　　　　　　　　2460/13 (2013.01)

(56) References Cited

U.S. PATENT DOCUMENTS

| | | | |
|---|---|---|---|
| 3,047,089 A | 7/1962 | Zwislocki | |
| D208,784 S | 10/1967 | Sanzone | |
| 3,586,794 A | 6/1971 | Michaelis | |
| 3,934,100 A | 1/1976 | Harada | |
| 3,983,336 A | 9/1976 | Malek et al. | |
| 4,069,400 A | 1/1978 | Johanson et al. | |
| 4,150,262 A | 4/1979 | Ono | |
| 4,334,315 A | 6/1982 | Ono et al. | |
| D266,271 S | 9/1982 | Johanson et al. | |
| 4,375,016 A | 2/1983 | Harada | |
| 4,588,867 A | 5/1986 | Konomi | |
| 4,617,429 A | 10/1986 | Bellafiore | |
| 4,654,883 A | 3/1987 | Iwata | |
| 4,682,180 A | 7/1987 | Gans | |
| 4,791,673 A | 12/1988 | Schreiber | |
| 4,852,177 A | 7/1989 | Ambrose | |
| 4,865,044 A | 9/1989 | Wallace et al. | |
| 4,984,277 A | 1/1991 | Bisgaard et al. | |
| 5,008,943 A | 4/1991 | Arndt et al. | |
| 5,185,802 A | 2/1993 | Stanton | |
| 5,191,602 A | 3/1993 | Regen et al. | |
| 5,201,007 A | 4/1993 | Ward et al. | |
| 5,201,008 A | 4/1993 | Arndt et al. | |
| D340,286 S | 10/1993 | Seo | |
| 5,280,524 A | 1/1994 | Norris | |
| 5,295,193 A | 3/1994 | Ono | |
| 5,298,692 A | 3/1994 | Ikeda et al. | |
| 5,343,532 A | 8/1994 | Shugart | |
| 5,347,584 A | 9/1994 | Narisawa | |
| 5,363,444 A | 11/1994 | Norris | |
| D367,113 S | 2/1996 | Weeks | |
| 5,497,339 A | 3/1996 | Bernard | |
| 5,606,621 A | 2/1997 | Reiter et al. | |
| 5,613,222 A | 3/1997 | Guenther | |
| 5,654,530 A | 8/1997 | Sauer et al. | |
| 5,692,059 A | 11/1997 | Kruger | |
| 5,721,783 A | 2/1998 | Anderson | |
| 5,748,743 A | 5/1998 | Weeks | |
| 5,749,072 A | 5/1998 | Mazurkiewicz et al. | |
| 5,771,438 A | 6/1998 | Palermo et al. | |
| D397,796 S | 9/1998 | Yabe et al. | |
| 5,802,167 A | 9/1998 | Hong | |
| D410,008 S | 5/1999 | Almqvist | |
| 5,929,774 A | 7/1999 | Charlton | |
| 5,933,506 A | 8/1999 | Aoki et al. | |
| 5,949,896 A | 9/1999 | Nageno et al. | |
| 5,987,146 A | 11/1999 | Pluvinage et al. | |
| 6,021,207 A | 2/2000 | Puthuff et al. | |
| 6,054,989 A | 4/2000 | Robertson et al. | |
| 6,081,724 A | 6/2000 | Wilson | |
| 6,084,526 A | 7/2000 | Blotky et al. | |
| 6,094,492 A | 7/2000 | Boesen | |
| 6,111,569 A | 8/2000 | Brusky et al. | |
| 6,112,103 A | 8/2000 | Puthuff | |
| 6,157,727 A | 12/2000 | Rueda | |
| 6,167,039 A | 12/2000 | Karlsson et al. | |
| 6,181,801 B1 | 1/2001 | Puthuff et al. | |
| 6,208,372 B1 | 3/2001 | Barraclough | |
| 6,230,029 B1 | 5/2001 | Yegiazaryan et al. | |
| 6,275,789 B1 | 8/2001 | Moser et al. | |
| 6,339,754 B1 | 1/2002 | Flanagan et al. | |
| D455,835 S | 4/2002 | Anderson et al. | |
| 6,408,081 B1 | 6/2002 | Boesen | |
| 6,424,820 B1 | 7/2002 | Burdick et al. | |
| D464,039 S | 10/2002 | Boesen | |
| 6,470,893 B1 | 10/2002 | Boesen | |
| D468,299 S | 1/2003 | Boesen | |
| D468,300 S | 1/2003 | Boesen | |
| 6,542,721 B2 | 4/2003 | Boesen | |
| 6,560,468 B1 | 5/2003 | Boesen | |
| 6,563,301 B2 | 5/2003 | Gventer | |
| 6,654,721 B2 | 11/2003 | Handelman | |
| 6,664,713 B2 | 12/2003 | Boesen | |
| 6,690,807 B1 | 2/2004 | Meyer | |
| 6,694,180 B1 | 2/2004 | Boesen | |
| 6,718,043 B1 | 4/2004 | Boesen | |
| 6,738,485 B1 | 5/2004 | Boesen | |
| 6,748,095 B1 | 6/2004 | Goss | |
| 6,754,358 B1 | 6/2004 | Boesen et al. | |
| 6,784,873 B1 | 8/2004 | Boesen et al. | |
| 6,823,195 B1 | 11/2004 | Boesen | |
| 6,852,084 B1 | 2/2005 | Boesen | |
| 6,879,698 B2 | 4/2005 | Boesen | |
| 6,892,082 B2 | 5/2005 | Boesen | |
| 6,920,229 B2 | 7/2005 | Boesen | |
| 6,952,483 B2 | 10/2005 | Boesen et al. | |
| 6,987,986 B2 | 1/2006 | Boesen | |
| 7,010,137 B1 | 3/2006 | Leedom et al. | |
| 7,113,611 B2 | 9/2006 | Leedom et al. | |
| D532,520 S | 11/2006 | Kampmeier et al. | |
| 7,136,282 B1 | 11/2006 | Rebeske | |
| 7,203,331 B2 | 4/2007 | Boesen | |
| 7,209,569 B2 | 4/2007 | Boesen | |
| 7,215,790 B2 | 5/2007 | Boesen et al. | |
| D549,222 S | 8/2007 | Huang | |
| D554,756 S | 11/2007 | Sjursen et al. | |
| 7,403,629 B1 | 7/2008 | Aceti et al. | |
| D579,006 S | 10/2008 | Kim et al. | |
| 7,463,902 B2 | 12/2008 | Boesen | |
| 7,508,411 B2 | 3/2009 | Boesen | |
| D601,134 S | 9/2009 | Elabidi et al. | |
| 7,825,626 B2 | 11/2010 | Kozisek | |
| 7,965,855 B1 | 6/2011 | Ham | |
| 7,979,035 B2 | 7/2011 | Griffin et al. | |
| 7,983,628 B2 | 7/2011 | Boesen | |
| D647,491 S | 10/2011 | Chen et al. | |
| 8,095,188 B2 | 1/2012 | Shi | |
| 8,108,143 B1 | 1/2012 | Tester | |
| 8,140,357 B1 | 3/2012 | Boesen | |
| D666,581 S | 9/2012 | Perez | |
| 8,300,864 B2 | 10/2012 | Müllenborn et al. | |
| 8,406,448 B2 | 3/2013 | Lin | |
| 8,430,817 B1 | 4/2013 | Al-Ali et al. | |
| 8,436,780 B2 | 5/2013 | Schantz et al. | |
| D687,021 S | 7/2013 | Yuen | |
| 8,679,012 B1 | 3/2014 | Kayyali | |
| 8,719,877 B2 | 5/2014 | VonDoenhoff et al. | |
| 8,774,434 B2 | 7/2014 | Zhao et al. | |
| 8,831,266 B1 | 9/2014 | Huang | |
| 8,891,800 B1 | 11/2014 | Shaffer | |
| 8,994,498 B2 | 3/2015 | Agrafioti et al. | |
| D728,107 S | 4/2015 | Martin et al. | |
| 9,013,145 B2 | 4/2015 | Castillo et al. | |
| 9,037,125 B1 | 5/2015 | Kadous | |
| D733,103 S | 6/2015 | Jeong et al. | |
| 9,081,944 B2 | 7/2015 | Camacho et al. | |
| 9,510,159 B1 | 11/2016 | Cuddihy et al. | |
| D773,439 S | 12/2016 | Walker | |
| D775,158 S | 12/2016 | Dong et al. | |
| D777,710 S | 1/2017 | Palmborg et al. | |
| 9,544,689 B2 | 1/2017 | Fisher et al. | |
| D788,079 S | 5/2017 | Son et al. | |
| 2001/0005197 A1 | 6/2001 | Mishra et al. | |
| 2001/0027121 A1 | 10/2001 | Boesen | |
| 2001/0043707 A1 | 11/2001 | Leedom | |
| 2001/0056350 A1 | 12/2001 | Calderone et al. | |
| 2002/0002413 A1 | 1/2002 | Tokue | |
| 2002/0007510 A1 | 1/2002 | Mann | |

(56) References Cited

U.S. PATENT DOCUMENTS

| | | |
|---|---|---|
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0147052 A1* | 7/2006 | Wikel ................... H04M 1/05 381/74 |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2007/0053544 A1* | 3/2007 | Jhao ................... H04M 1/6066 381/384 |
| 2008/0076972 A1 | 3/2008 | Dorogusker et al. |
| 2008/0090622 A1 | 4/2008 | Kim et al. |
| 2008/0146890 A1 | 6/2008 | LeBoeuf et al. |
| 2008/0187163 A1 | 8/2008 | Goldstein et al. |
| 2008/0253583 A1 | 10/2008 | Goldstein et al. |
| 2008/0254780 A1 | 10/2008 | Kuhl et al. |
| 2008/0255430 A1 | 10/2008 | Alexandersson et al. |
| 2008/0298606 A1 | 12/2008 | Johnson et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0073070 A1 | 3/2009 | Rofougaran |
| 2009/0097689 A1 | 4/2009 | Prest et al. |
| 2009/0105548 A1 | 4/2009 | Bart |
| 2009/0154739 A1 | 6/2009 | Zellner |
| 2009/0191920 A1 | 7/2009 | Regen et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2010/0033313 A1 | 2/2010 | Keady et al. |
| 2010/0150383 A1* | 6/2010 | Sampat ..................... H04R 1/10 381/311 |
| 2010/0203831 A1 | 8/2010 | Muth |
| 2010/0210212 A1 | 8/2010 | Sato |
| 2010/0245585 A1* | 9/2010 | Fisher ................... H04M 1/6066 348/164 |
| 2010/0320961 A1 | 12/2010 | Castillo et al. |
| 2011/0140844 A1 | 6/2011 | McGuire et al. |
| 2011/0187640 A1* | 8/2011 | Jacobsen ............... G02B 27/017 345/156 |
| 2011/0206217 A1* | 8/2011 | Weis ................... H04M 1/6066 381/74 |
| 2011/0222701 A1* | 9/2011 | Donaldson ........... H04R 1/1083 381/74 |
| 2011/0239497 A1 | 10/2011 | McGuire et al. |
| 2011/0286615 A1 | 11/2011 | Olodort et al. |
| 2012/0057740 A1 | 3/2012 | Rosal |
| 2012/0140973 A1* | 6/2012 | Olodort ................ H04R 1/1066 381/375 |
| 2012/0155670 A1 | 6/2012 | Rutschman |
| 2012/0309453 A1 | 12/2012 | Maguire |
| 2013/0093852 A1* | 4/2013 | Ye ............................ A61H 3/061 348/46 |
| 2013/0106454 A1 | 5/2013 | Liu et al. |
| 2013/0148818 A1* | 6/2013 | Yamkovoy ........... H04R 1/1041 381/74 |
| 2013/0316642 A1 | 11/2013 | Newham |
| 2013/0346168 A1 | 12/2013 | Zhou et al. |
| 2014/0004912 A1 | 1/2014 | Rajakarunanayake |
| 2014/0014697 A1 | 1/2014 | Schmierer et al. |
| 2014/0020089 A1 | 1/2014 | Perini, II |
| 2014/0072136 A1 | 3/2014 | Tenenbaum et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0146973 A1 | 5/2014 | Liu et al. |
| 2014/0153768 A1 | 6/2014 | Hagen et al. |
| 2014/0163771 A1 | 6/2014 | Demeniuk |
| 2014/0185828 A1* | 7/2014 | Helbling ................. H03G 5/165 381/103 |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270234 A1* | 9/2014 | Beal ..................... H04R 1/1025 381/74 |
| 2014/0270271 A1 | 9/2014 | Dehe et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0035643 A1 | 2/2015 | Kursun |
| 2015/0036835 A1* | 2/2015 | Chen ..................... H04R 1/1041 381/74 |
| 2015/0110587 A1 | 4/2015 | Hori |
| 2015/0148989 A1 | 5/2015 | Cooper et al. |
| 2015/0181356 A1 | 6/2015 | Krystek et al. |
| 2015/0245127 A1 | 8/2015 | Shaffer |
| 2015/0264472 A1 | 9/2015 | Aase |
| 2015/0264501 A1 | 9/2015 | Hu et al. |
| 2015/0358751 A1 | 12/2015 | Deng et al. |
| 2015/0359436 A1 | 12/2015 | Shim et al. |
| 2015/0373467 A1 | 12/2015 | Gelter |
| 2015/0373474 A1 | 12/2015 | Kraft et al. |
| 2016/0033280 A1 | 2/2016 | Moore et al. |
| 2016/0034249 A1 | 2/2016 | Lee et al. |
| 2016/0071526 A1 | 3/2016 | Wingate et al. |
| 2016/0072558 A1 | 3/2016 | Hirsch et al. |
| 2016/0073189 A1 | 3/2016 | Lindén et al. |
| 2016/0125892 A1 | 5/2016 | Bowen et al. |
| 2016/0162259 A1 | 6/2016 | Zhao et al. |
| 2016/0173968 A1* | 6/2016 | Fargeau ................ H04R 1/1016 381/375 |
| 2016/0209691 A1 | 7/2016 | Yang et al. |
| 2016/0324478 A1 | 11/2016 | Goldstein |
| 2016/0353196 A1 | 12/2016 | Baker et al. |
| 2016/0360350 A1 | 12/2016 | Watson et al. |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0078780 A1 | 3/2017 | Qian et al. |
| 2017/0078785 A1 | 3/2017 | Qian et al. |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0127168 A1 | 5/2017 | Briggs et al. |

(56) References Cited

U.S. PATENT DOCUMENTS

| | | |
|---|---|---|
| 2017/0131094 A1 | 5/2017 | Kulik |
| 2017/0142511 A1 | 5/2017 | Dennis |
| 2017/0146801 A1 | 5/2017 | Stempora |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0193978 A1 | 7/2017 | Goldman |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0251933 A1 | 9/2017 | Braun et al. |
| 2017/0257698 A1 | 9/2017 | Boesen et al. |
| 2017/0263236 A1 | 9/2017 | Boesen et al. |
| 2017/0273622 A1 | 9/2017 | Boesen |
| 2017/0280257 A1 | 9/2017 | Gordon et al. |
| 2017/0366233 A1 | 12/2017 | Hviid et al. |
| 2017/0366889 A1* | 12/2017 | Schipper ............... H04R 1/086 |
| 2018/0007994 A1 | 1/2018 | Boesen et al. |
| 2018/0008194 A1 | 1/2018 | Boesen |
| 2018/0008198 A1 | 1/2018 | Kingscott |
| 2018/0009447 A1 | 1/2018 | Boesen et al. |
| 2018/0011006 A1 | 1/2018 | Kingscott |
| 2018/0011682 A1 | 1/2018 | Milevski et al. |
| 2018/0011994 A1 | 1/2018 | Boesen |
| 2018/0012228 A1 | 1/2018 | Milevski et al. |
| 2018/0013195 A1 | 1/2018 | Hviid et al. |
| 2018/0014102 A1 | 1/2018 | Hirsch et al. |
| 2018/0014103 A1 | 1/2018 | Martin et al. |
| 2018/0014104 A1 | 1/2018 | Boesen et al. |
| 2018/0014107 A1 | 1/2018 | Razouane et al. |
| 2018/0014108 A1 | 1/2018 | Dragicevic et al. |
| 2018/0014109 A1 | 1/2018 | Boesen |
| 2018/0014113 A1 | 1/2018 | Boesen |
| 2018/0014140 A1 | 1/2018 | Milevski et al. |
| 2018/0014436 A1 | 1/2018 | Milevski |
| 2018/0034951 A1 | 2/2018 | Boesen |
| 2018/0040093 A1 | 2/2018 | Boesen |

FOREIGN PATENT DOCUMENTS

| | | | |
|---|---|---|---|
| CN | 104837094 A | | 8/2015 |
| EP | 1469659 A1 | | 10/2004 |
| EP | 1017252 A3 | | 5/2006 |
| EP | 2903186 A1 | | 8/2015 |
| GB | 2074817 | | 4/1981 |
| GB | 2508226 A | | 5/2014 |
| JP | 06292195 | | 10/1998 |
| WO | 2008103925 A1 | | 8/2008 |
| WO | 2008113053 A1 | | 9/2008 |
| WO | 2007034371 A3 | | 11/2008 |
| WO | 2011001433 A2 | | 1/2011 |
| WO | 2012071127 A1 | | 5/2012 |
| WO | 2013134956 A1 | | 9/2013 |
| WO | 2014046602 A1 | | 3/2014 |
| WO | 2014043179 A3 | | 7/2014 |
| WO | 2015061633 A2 | | 4/2015 |
| WO | 2015110577 A1 | | 7/2015 |
| WO | 2015110587 A1 | | 7/2015 |
| WO | 2016032990 A1 | | 3/2016 |
| WO | 2016187869 A1 | | 12/2016 |

OTHER PUBLICATIONS

Update From BRAGI—$3,000,000—Yipee (Mar. 22, 2014).

Wertzner et al., "Analysis of fundamental frequency, jitter, shimmer and vocal intensity in children with phonological disorders", V. 71, n.5, 582-588, Sep./Oct. 2005; Brazilian Journal of Othrhinolaryngology.

Wikipedia, "Gamebook", https://en.wikipedia.org/wiki/Gamebook, Sep. 3, 2017, 5 pages.

Wikipedia, "Kinect", "https://en.wikipedia.org/wiki/Kinect", 18 pages, (Sep. 9, 2017).

Wikipedia, "Wii Balance Board", "https://en.wikipedia.org/wiki/Wii_Balance_Board", 3 pages, (Jul. 20, 2017).

Akkermans, "Acoustic Ear Recognition for Person Identification", Automatic Identification Advanced Technologies, 2005 pp. 219-223.

Alzahrani et al: "A Multi-Channel Opto-Electronic Sensor to Accurately Monitor Heart Rate against Motion Artefact during Exercise", Sensors, vol. 15, No. 10, Oct. 12, 2015, pp. 25681-25702, XPO55334602, DOI: 10.3390/s151025681 the whole document.

Announcing the $3,333,333 Stretch Goal (Feb. 24, 2014).

Ben Coxworth: "Graphene-based ink could enable low-cost, foldable electronics", "Journal of Physical Chemistry Letters", Northwestern University, (May 22, 2013).

Blain: "World's first graphene speaker already superior to Sennheiser MX400", htt://www.gizmag.com/graphene-speaker-beats-sennheiser-mx400/31660, (Apr. 15, 2014).

BMW, "BMW introduces BMW Connected—The personalized digital assistant", "http://bmwblog.com/2016/01/05/bmw-introduces-bmw-connected-the-personalized-digital-assistant", (Jan. 5, 2016).

BRAGI is on Facebook (2014).

BRAGI Update—Arrival of Prototype Chassis Parts—More People—Awesomeness (May 13, 2014).

BRAGI Update—Chinese New Year, Design Verification, Charging Case, More People, Timeline(Mar. 6, 2015).

BRAGI Update—First Sleeves From Prototype Tool—Software Development Kit (Jun. 5, 2014).

BRAGI Update—Let's Get Ready to Rumble, A Lot to Be Done Over Christmas (Dec. 22, 2014).

BRAGI Update—Memories From April—Update on Progress (Sep. 16, 2014).

BRAGI Update—Memories from May—Update on Progress—Sweet (Oct. 13, 2014).

BRAGI Update—Memories From One Month Before Kickstarter—Update on Progress (Jul. 10, 2014).

BRAGI Update—Memories From the First Month of Kickstarter—Update on Progress (Aug. 1, 2014).

BRAGI Update—Memories From the Second Month of Kickstarter—Update on Progress (Aug. 22, 2014).

BRAGI Update—New People @BRAGI—Prototypes (Jun. 26, 2014).

BRAGI Update—Office Tour, Tour to China, Tour to CES (Dec. 11, 2014).

BRAGI Update—Status on Wireless, Bits and Pieces, Testing—Oh Yeah, Timeline(Apr. 24, 2015).

BRAGI Update—The App Preview, The Charger, The SDK, BRAGI Funding and Chinese New Year (Feb. 11, 2015).

BRAGI Update—What We Did Over Christmas, Las Vegas & CES (Jan. 19, 2014).

BRAGI Update—Years of Development, Moments of Utter Joy and Finishing What We Started(Jun. 5, 2015).

BRAGI Update—Alpha 5 and Back to China, Backer Day, on Track(May 16, 2015).

BRAGI Update—Beta2 Production and Factory Line(Aug. 20, 2015).

BRAGI Update—Certifications, Production, Ramping Up.

(56) References Cited

OTHER PUBLICATIONS

BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2015).
BRAGI Update—On Track, Design Verification, How It Works and What's Next(Jul. 15, 2015).
BRAGI Update—On Track, on Track and Gems Overview.
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Healthcare Risk Management Review, "Nuance updates computer-assisted physician documentation solution" (Oct. 20, 2016).
Hoffman, "How to Use Android Beam to Wirelessly Transfer Content Between Devices", (Feb. 22, 2013).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces a Health + Mobility Concept for Wellness in Mobility", Fountain Valley, Califorma (2017).
International Search Report & Written Opinion, PCT/EP16/70245 (dated Nov. 16, 2016).
International Search Report & Written Opinion, PCT/EP2016/070231 (dated Nov. 18, 2016).
International Search Report & Written Opinion, PCT/EP2016/070247 (dated Nov. 18, 2016).
Jain A et al: "Score normalization in multimodal biometric systems", Pattern Recognition, Elsevier, GB, vol. 38, No. 12, Dec. 31, 2005, pp. 2270-2285, XPO27610849, ISSN: 0031-3203.
Last Push Before the Kickstarter Campaign Ends on Monday 4pm CET (Mar. 28, 2014).
Niemanja Paunovic et al, "A methodology for testing complex professional electronic systems", Serbian Journal of Electrical Engineering, vol. 9, No. 1, Feb. 1, 2012, pp. 71-80, XPO55317584, YU.
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Nuance, "ING Netherlands Launches Voice Biometrics Payment System in the Mobile Banking App Powered by Nuance", "https://www.nuance.com/about-us/newsroom/press-releases/ing-netherlands-launches-nuance-voice-biometrics.html", 4 pages (Jul. 28, 2015).
Staab, Wayne 1, et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for the Dash (Feb. 12, 2014).
Stretchgoal—Windows Phone Support (Feb. 17, 2014).
The Dash + The Charging Case & The BRAGI News (Feb. 21, 2014).

* cited by examiner

INTELLIGENT WIRELESS HEADSET SYSTEM

PRIORITY STATEMENT

This application claims priority to U.S. Provisional Patent Application No. 62/456,548, filed on Feb. 8, 2017, titled Headset all of which is hereby incorporated by reference in its entirety.

FIELD OF THE INVENTION

The present invention relates to wearable devices. Particularly, the present invention relates to electronic wearable devices. More particularly, but not exclusively, the present invention relates to an intelligent wireless headset.

BACKGROUND

When wireless/cellular phone technology was initially commercialized, cellular phones were voice-only communication devices (i.e. such devices did not have any capability beyond voice communication). These cellular phones were hand-held devices. A hands-free option was introduced requiring plugging in a wired headset connection between the phone and an earpiece and microphone. Over time, some new technologies evolved.

Most notably, Bluetooth® Communication Protocol for short-range wireless communications enabling wireless devices to communicate with each other over short distances. With the introduction of the Bluetooth communication protocol, the wireless phones could communicate with other devices over a short range. This advancement in technology created a new market for wireless accessories. The very nature of the protocol eliminated the need for a wired device to establish hands-free operation. Now, the user could use a cellular phone to communicate with an accessory (or any other device) over a wireless network, thus truly making the use of the device hands-free.

Digital Video Camera and Streaming: With the advent of digital imaging cameras a user could capture and store images and videos in a digital format. The next step in the evolution of the video cameras was their ability to stream the video over wireless networks. Modern day cameras also have built-in GPS capabilities.

Wearable cameras such as helmet cams began as bulky still image and video cameras often bolted into athletes' helmets. With the onset of digital video recording and flash memory came a new generation of what has been referred to as lipstick or bullet cameras smaller and lighter and were either wired to an external digital recorder or incorporated some embedded or removable flash memory storage. The next generation of wearable cameras introduced wireless data transmission such as Bluetooth for wireless uploading of stored still image and video files and/or Wireless IP Cameras offering outgoing video streaming to the Internet via a Wireless Local Area Network or wired or wireless video streaming and networking via an external digital recorder or intelligent paired computing and wide or local area networking device such as a smart phone or personal computer.

The hands-free wireless video camera telecommunications headset represents a new generation of entirely autonomous wearable two-way and multi-feed hands-free wireless communications devices capable of sending and receiving voice data, and audio-video without the need for a paired external, handheld, wired or wireless computing, networking or storage device.

Headsets and headsets are widely used for listening to music and other purposes. However, headsets and headsets isolate a user from ambient sounds and have limited functionality and usefulness. What is needed is an intelligent wireless headset with improved functionality.

SUMMARY

Therefore, it is a primary object, feature, or advantage of the present invention to improve over the state of the art.

An intelligent wireless headset in embodiments of the present invention may have one or more of the following features: (a) a left ear portion having at least one microphone and at least one speaker associated therewith, (b) a right ear portion having at least one microphone and at least one speaker associated therewith, (c) a connecting band between the left ear portion and the right ear portion, (d) a wireless radio transceiver disposed within the intelligent wireless headset, (e) a cellular transceiver disposed within the intelligent wireless headset, (f) a gestural interface disposed within the intelligent wireless headset, (g) a processor disposed within the intelligent wireless headset and operatively connected to the at least one microphone of the left ear portion, the at least one speaker of the left ear portion, the at least one microphone of the right ear portion, and the at least one speaker of the right ear portion; wherein the processor is configured to process the ambient sound from the left ear portion and the ambient sound from the right ear portion and reproduce a processed version of the ambient sound from the left ear portion at the at least one speaker of the left ear portion and a processed version of the ambient sound from the right ear portion at the at least one speaker of the right ear portion, (h) at least one imaging sensor mounted on the right ear portion, (i) at least one imaging sensor mounted on the left ear portion, (j) a left ear cushion on an interior portion of the left ear portion, (k) a right ear cushion on an interior portion of the right ear portion, (l) a left hard exterior surface at an exterior portion of the left ear portion, (m) a right hard exterior surface at an exterior portion of the right ear portion, wherein the gestural interface receives gestures from the user at the left hard exterior surface and the right hard exterior surface using optical detectors, (n) a plurality of microphones arranged along the connecting band.

An intelligent wireless headset system in embodiments of the current invention may have one or more of the following features: (a) a left ear portion having at least one microphone and at least one speaker associated therewith, (b) a right ear portion having at least one microphone and at least one speaker associated therewith, (c) a connecting band between the left ear portion and the right ear portion, (d) a wireless radio transceiver disposed within the intelligent wireless headset, (e) a cellular transceiver disposed within the intelligent wireless headset, and (f) a headset charger capable of receiving the intelligent wireless headset system.

An intelligent wireless headset system in embodiments of the present invention may have one or more of the following features: (a) a left ear portion having at least one microphone and at least one speaker associated therewith, (b) a right ear portion having at least one microphone and at least one speaker associated therewith, (c) a connecting band between the left ear portion and the right ear portion, (d) a wireless radio transceiver disposed within the intelligent wireless headset, (e) a cellular transceiver disposed within the intelligent wireless headset, (f) a headset network capable of operably coupling the intelligent wireless headset with at least one device in the headset network, (g) sensors to collect biometric information, (h) a camera for collecting video information, (i) outer speakers located on the housing, and (j) a memory for storing biometric information.

One or more of these and/or other objects, features, or advantages of the present invention will become apparent from the specification and claims follow. No single embodiment need provide every object, feature, or advantage. Different embodiments may have different objects, features, or advantages. Therefore, the present invention is not to be limited to or by any objects, features, or advantages stated herein.

DETAILED DESCRIPTION

The following discussion is presented to enable a person skilled in the art to make and use the present teachings. Various modifications to the illustrated embodiments will be clear to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings. While embodiments of the present invention are discussed in terms of headsets, it is fully contemplated embodiments of the present invention could be used in most any wearable electronic device without departing from the spirit of the invention.

It is an object, feature, or advantage of the present invention to provide an intelligent wireless headset which may be used to better detect user voice sound information.

It is still a further object, feature or advantage of the present invention to provide an intelligent wireless headset which allows for ambient sound to pass through even when a user's ears are isolated from the environment.

Another object, feature, or advantage is to provide an intelligent wireless headset which allows a user to communicate with the headset through gestures.

Yet another object, feature, or advantage is to provide an intelligent wireless headset which may capture visual information to better interact with a user or assist the user in interacting with their environment.

A further object, feature, or advantage is to provide an intelligent wireless headset which may be used as a speaker and for conference calls.

The present invention relates to an intelligent wireless headset. The intelligent wireless headset may be used for any number of purposes. These include listening to music, talking on the phone, playing games or other purposes.

The intelligent wireless headset may include a left ear portion, a right ear portion and a connecting band between the left ear portion and the right ear portion. Electric conductors may be present which electrically connect circuits or components within the left ear portion with circuits or components within the right ear portion or with components or circuits positioned along the connecting band. Each of the left ear portion and the right ear portion may include an ear cushion or pad positioned on the interior thereof and a housing at the external portion thereof. The housing may contain electronic components, batteries and circuitry. In addition, a surface of the housing may be used to receive gestures from the user. For example, optical detectors positioned at the housing may be used to detect gestures of a user such as swipes, taps, holds, or other gestures as a part of a gestural interface. These gestures may be performed to interact with the intelligent wireless headset. Other types of touch sensors may be used instead of or in addition to optical detectors. For example, capacitive sensors may be used.

One or more inertial sensors may be present in the wireless headset. The inertial sensors may be used to detect movements by a user including heading movements. Thus, for example, a user may nod their head, shake their head or otherwise perform other head movements which may be detected by the one or more inertial sensors and interpreted. For example, in some contexts, a nodding of the head may be interpreted a "YES" or an affirmative response while the shaking of the head from side to side may be interested as a "NO" or negative response.

One or more physiological sensors such as pulse oximeters or other optical sensors may be present on the left ear portion, the right ear portion or the band connecting the left ear portion and the right ear portion.

The intelligent wireless headset may include one or more microphones on each of the left ear portion and the right ear portion. At least one of the microphones on each side may be outward facing and used to detect ambient or external audio. One or more microphones may also be positioned interiorly preferably against the skull of the user to detect bone vibrations such as those which occur when the user speaks. Being able to detect sounds in multiple locations is advantageous for a variety of reasons including the ability to separate ambient sound from voice sound of a user such as who may be using the headset to take or place a call.

Although the user's ears are isolated from external sounds while wearing the headset or headsets, the intelligent wireless headset may also allow for passthrough of audio sounds by reproducing sound detected with the one or more external-facing microphones internally. Such passthrough may occur with or without additional processing such as to modify volume, filter out noise, emphasize sounds of interest or otherwise. The additional processing may allow for detection, classification, and/or extraction of sounds of interest.

A first wireless transceiver such as a Bluetooth transceiver or BLE transceiver may be positioned within the intelligent wireless headset. A second wireless transceiver such as a Wi-Fi transceiver may also be present. In addition, a cellular transceiver may be positioned within the left ear portion, the right ear portion, and/or the band connecting the left ear portion and the right ear portion.

A plurality of microphones may be positioned in the headset including in the left ear portion, the right ear portion, or the band connecting the left ear portion and the right ear portion. The microphones may include an array of microphones which may be used in beam forming or in other applications.

In one application the wireless headset is used during a conference call. The headset may, for example, be placed on a conference room table. The headset may have an array of microphones. The array of microphones may be positioned along the band. Beam-forming allows for better detection of the voice of different individuals around the conference room. In this application, a speaker of the wireless headset may be used. Thus, the headset may be worn by a user and with the built-in cellular communications (or Wi-Fi where VoIP or other voice conferencing protocols are used) for private conversations or removed and shared where communications wish to be shared with other people.

Another use of a microphone in the top headband is this may be used when an individual is wearing the headset and another individual facing them is speaking to them. For example, the user wearing the headset may be working in a manufacturing environment where machines are being operated which generate loud noises. Wearing the headset provides a form of hearing protection for the user. However, if another individual walks up to the user and speaks with the user, the user may want to hear what the other individual is saying. Thus, an audio passthrough mode may be used to reproduce the person's voice. Active noise cancellation may be performed to eliminate the ambient noise. The presence of multiple microphones assists with this.

Where cameras are used, the cameras may be time-of-flight (ToF) cameras which are range imaging camera systems used to resolve distance based on the known speed of light by measuring the time-of-flight of a light signal between the camera and the object for each point of the image. A time-of-flight camera is one form of a scanner less LIDAR system in which an entire scene may be captured with a laser or light pulse. Information obtained from the time-of-flight camera may be used for many different purposes. For example, such information may be used to map a room and/or to identify the location or relative location of sound sources. Such information may then be used in performing audio processing or for other purposes.

It is to be further understood more than one camera may be present, including more than one time-of-flight camera. For example, one camera may be on the left ear portion and one camera may be on the right ear portion to provide for stereo imaging. It is to be further understood because the distance between such cameras would be greater than the distance between the eyes of an individual (for an even larger than stereo view), image processing may take this into account including to adjust the imaging to match an individual person's experience based on the distance between their eyes. Thus, for example, post-processing may be performed to accomplish this objective. Also, or instead of a left forward-facing camera and a right forward-facing camera, there may be a left rear facing camera and a right rear facing camera. In addition, there may be one or more side facing cameras on the left and/or right.

It is to also be understood control may be performed through sensing of gestures using one or more cameras. For example, a user may make hand gestures which are detected by one or more of the cameras and this information may be processed to identify the hand gestures being performed by the user and interpret the gestures. The gestures may be used to perform a command or to furnish information in response to a prompt for information or instruction from the user. Similarly, changes in the view from one or more cameras may be used to determine head gestures performed by the user or to determine the direction in which the head of the user is facing. This contextual information may be used for a variety of different purposes to better interact with the environment of the user. Thus, for example, this information may be used to assist in identifying a sound source of interest to the user.

The use of the cameras may have any number of other applications to replace or augment the perceptions of a user. In one embodiment, the cameras may be used in a system which assists a blind or vision-impaired person by identifying obstacles in their path and providing indicative audio feedback. The audio feedback may be in the form of tones or changing tones or may be in the form of voice feedback or instructions. Or other types of feedback audio or otherwise may be used.

Figure 1:
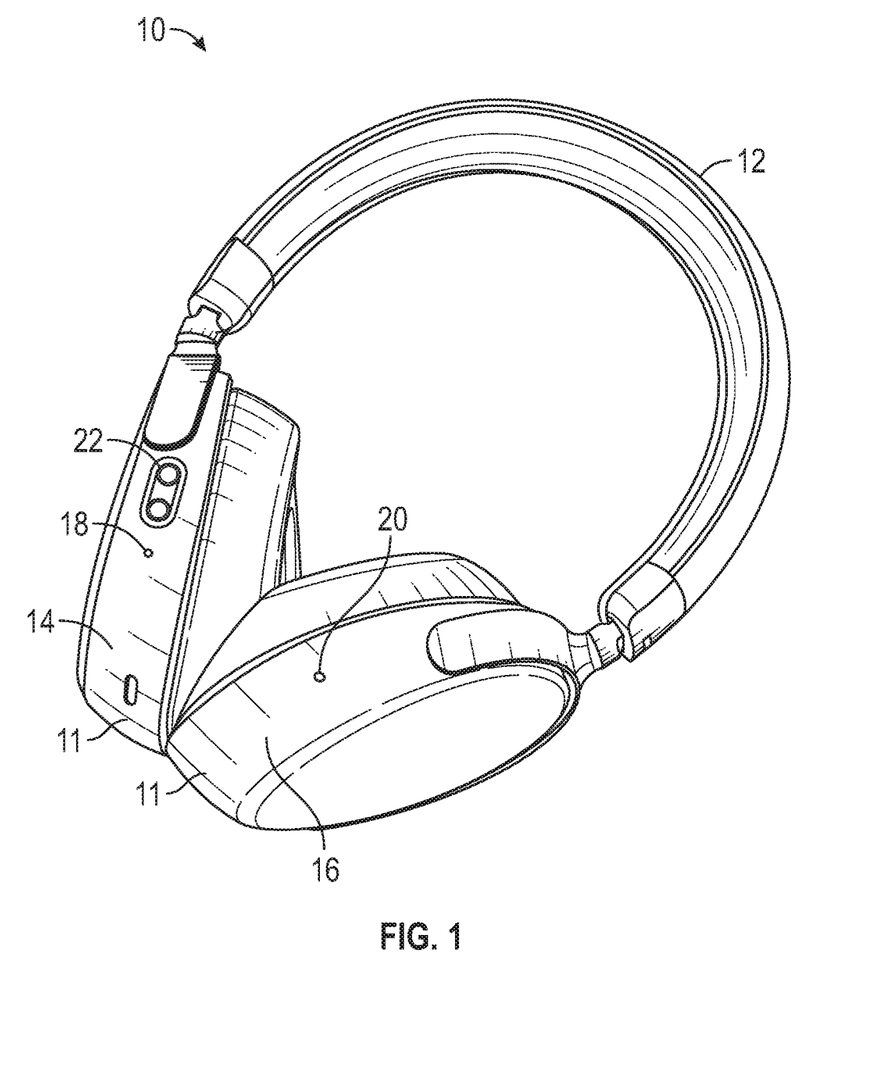
FIG. 1 is a pictorial view of an intelligent headset in accordance with embodiments of the present invention.

FIG. 1 illustrates one embodiment of an intelligent headset 10. The intelligent headset 10 has a left ear portion 14 having at least one microphone 18 and at least one speaker associated therewith. The intelligent headset 10 further includes a right ear portion 16 having at least one microphone 20 and at least one speaker associated therewith. There is a connecting band 12 between the left ear portion 14 and the right ear portion 16. Various components are disposed within the intelligent headset (in the left ear portion, right ear portion, and/or the connecting band). This includes cell phone circuitry including a cellular transceiver, one or more wireless transceivers such as a Bluetooth or BLE transceiver and/or a Wi-Fi transceiver, one or more processors, sensors, and other components. A camera module 22 is shown which may include a flash. It is to be understood however, more than one camera module 22 may be present on one or both, or all the left ear portion 14, the right ear portion 16, and the connecting band 12. A left hard exterior surface may be positioned at an exterior portion of the left ear portion. A right hard exterior surface may be positioned at an exterior portion of the right ear portion. Optical detectors may be placed at these surfaces to detect touches by a user. Alternatively, capacitive touch sensors may be used. Touch sensors of any kind may form a portion of a gestural interface receiving gestures from the user at the left hard exterior surface and the right hard exterior surface using optical detectors. These gestures may include taps, holds, swipes, or other types of gestures. Any number of other sensors shown or described throughout may be positioned on one or more of the left ear portion, right ear portion, or connecting band.

Left 14 and right 16 ear portions have a housing 11. The housing 11 may be composed of plastic, metallic, nonmetallic or any material or combination of materials having substantial deformation resistance to facilitate energy transfer if a sudden force is applied to the left or right ear portions 14 & 16. For example, if headset 10 is dropped by a user, the housing 11 may transfer the energy received from the surface impact throughout the entire headset 10. In addition, the housing 11 may be capable of a degree of flexibility to facilitate energy absorbance if one or more forces is applied to the headset 10. For example, if an object is dropped on the headset 10, the housing 11 may bend to absorb the energy from the impact so the components within the headset 10 are not substantially damaged. The flexibility of the housing 11 should not, however, be flexible to the point where one or more components of the headset 10 may become nonfunctional if one or more forces is applied to the headset 10.

Microphones 18 & 20 are operably coupled to the housing 11 and the processor 40 and are positioned to receive ambient sounds. The ambient sounds may originate from an object worn or carried by a user, a third party, or the environment. Environmental sounds may include natural sounds such as thunder, rain, or wind or artificial sounds such as sounds made by machinery at a construction site. The type of microphones 18 & 20 employed may be a directional, bidirectional, omnidirectional, cardioid, shotgun, or one or more combinations of microphone types, and more than one microphone may be present in the headset 10. If more than one microphone is employed, each microphone 18 & 20 may be arranged in any configuration conducive to receiving an ambient sound. In addition, each microphone 18 & 20 may comprise an amplifier and/or an attenuator configured to modify sounds by either a fixed factor or in accordance with one or more user settings of an algorithm stored within a memory or the processor 40 of the headset 10. For example, a user may issue a voice command to the headset 10 via the microphones 18 & 20 to instruct the headset 10 to amplify sounds having sound profiles substantially like a human voice and attenuate sounds exceeding a certain sound intensity. The user may also modify the user settings of the headset 10 using a voice command received by one of the microphones 18 & 20, a control panel or gestural interface on the headset 10, or a software application stored on an external electronic device such as a mobile phone or a tablet capable of interfacing with the headset 10. Sounds may also be amplified or attenuated by an amplifier or an attenuator operably coupled to the headset 10 and separate from the microphones 18 & 20 before being communicated to the processor 40 for sound processing.

Figure 2:
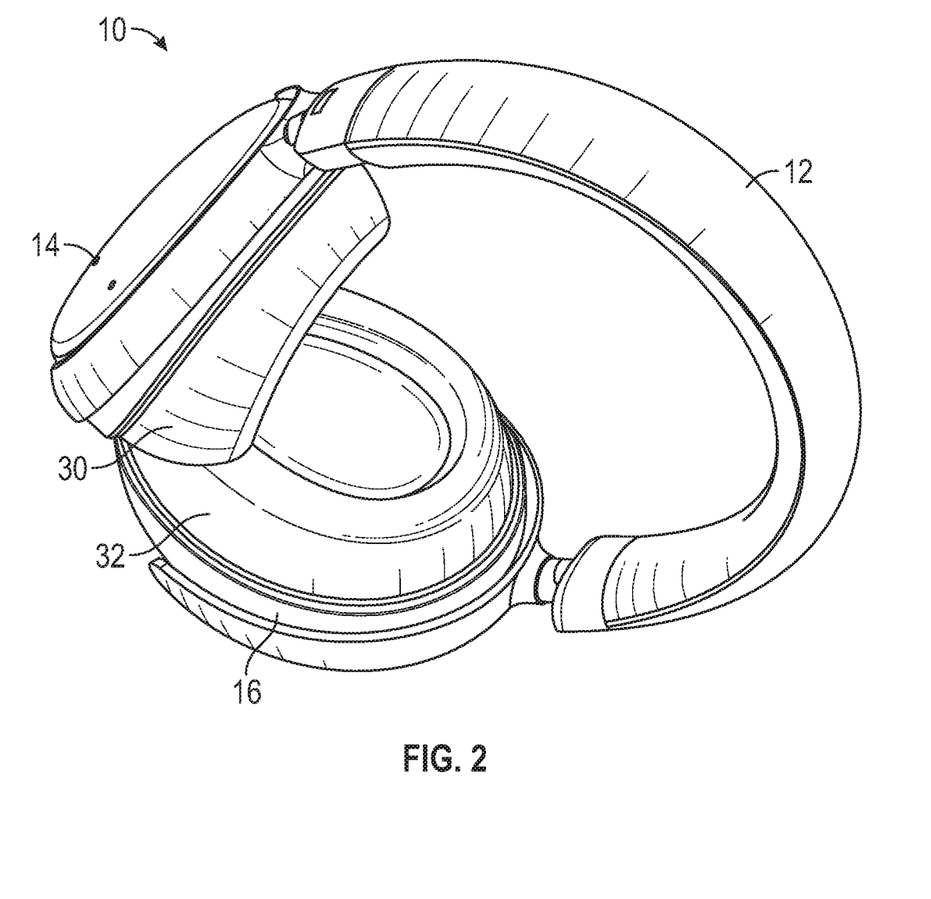
FIG. 2 is a pictorial view of the intelligent headset in accordance with embodiments of the present invention.

FIG. 2 illustrates another view of the intelligent headset 10 with a left ear cushion 30 and a right ear cushion 32. The left ear cushion 30 may be positioned on an interior portion of the left ear portion 14 and the right ear cushion 32 may be positioned on an interior portion of the right ear portion 16.

Figure 3:
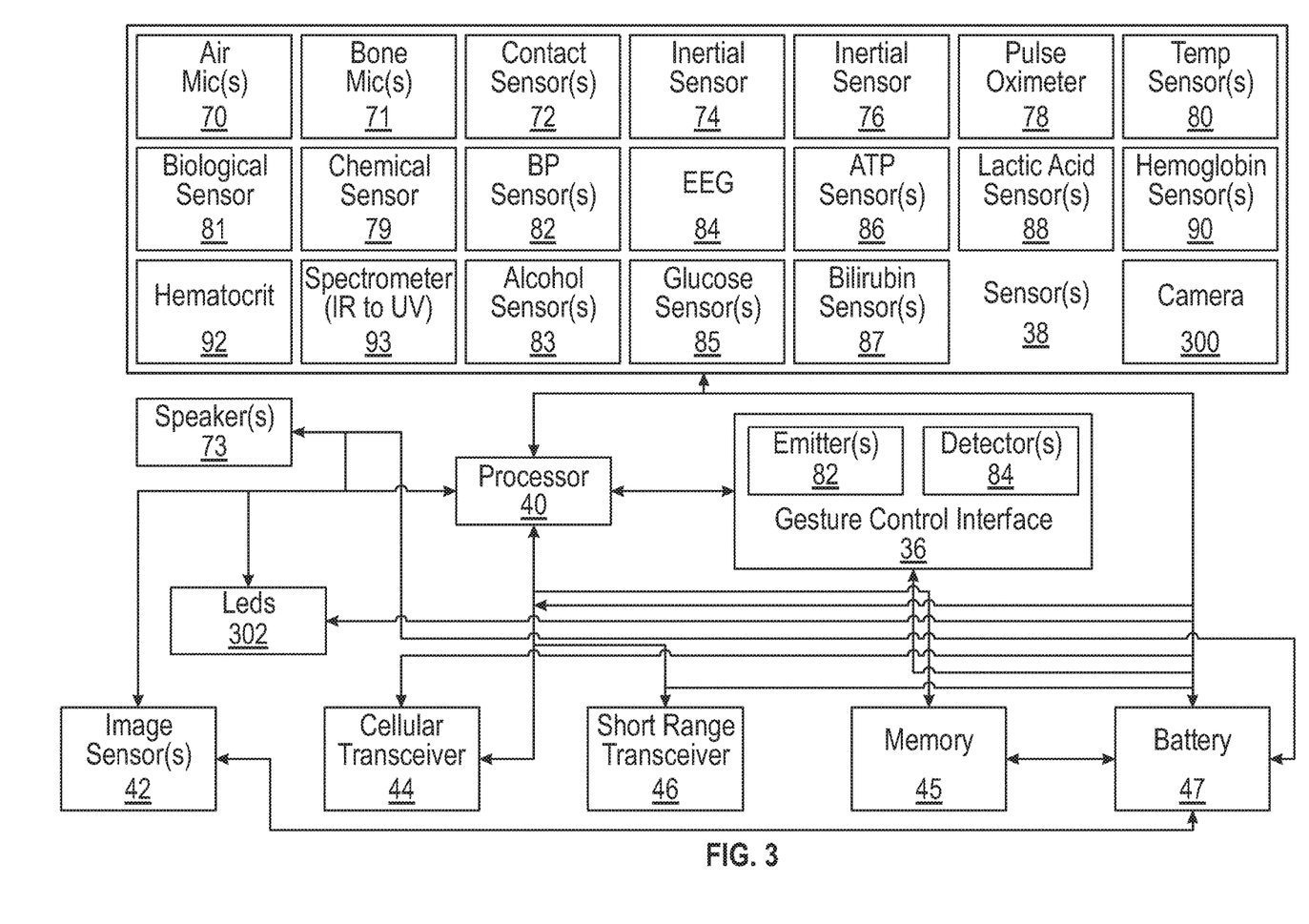
FIG. 3 is a block diagram of one embodiment of an intelligent headset in accordance with embodiments of the present invention.

FIG. 3 is a block diagram illustrating one embodiment of an intelligent wireless headset. A plurality of sensors 38 are shown. This may include one or more air microphones 70, bone microphones 70, one or more contact sensors 72 which may be used to assist in determining if a user is wearing the intelligent headset. The one or more sensors 38 may further include one or more inertial sensors 74, 76, a pulse oximeter 78, one or more temperature sensors 80, one or more biological sensors 81, one or more chemical sensors 79, one or more blood pressure sensors 82, one or more EEG sensors 84, one or more ATP sensors 86, one or more lactic acid sensors 88, one or more hemoglobin sensors 90, one or more hematocrit sensors 92, one or more spectrometers 93, one or more alcohol sensors 83, one or more glucose sensors 95, one or more bilirubin sensors 87, or other types of sensors. Note the ear portions cover the ears and thus a biologically rich area for various types of biological sensors. In addition, the headset spans the head to provide additional locations for sensors.

All the sensors 38 may be operatively connected to a processor 40 which may include one or more processors as well as appropriate signal conditioning, conversions and processing. Also, operatively connected to the processor 40 are speakers 73 which may include one or more speakers in the left ear piece portion and the right ear piece portion. A gesture control interface 36 is also operatively connected to the processor 40. The gesture control system may include one or more emitters 82 and one or more detectors 84. Also, operatively connected to the processor 40 are one or more image sensors 42. The image sensors 42 may include one or more cameras including time of flight sensors at the left ear portion, the right ear portion, and/or the connecting band. A cellular transceiver 44 is also disposed within the intelligent headset and may be used for making or receiving cellular voice calls and/or communicating data over a cellular network. One or more short range transceivers 46 may also be present and be operatively connected to the intelligent control system. The one or more short range transceivers may include one or more of a Bluetooth® transceiver, a BLE transceiver, a Wi-Fi transceiver, or other types of transceivers.

Speakers 73 are operably coupled to the housing 11 and the processor 40. The speakers 73 may produce ambient sounds modified by the processor 40 or one or more additional components of the headset 10. The modified ambient sounds produced by the speaker 73 may include modified sounds made by an object worn or carried by the user, one or more amplified human voices, one or more attenuated human voices, one or more amplified environmental sounds, one or more attenuated environmental sounds or a combination of one or more of the modified sounds. In addition, the speakers 73 may produce additional sounds such as music or a sporting event either stored within a memory of the headset 10 or received from a third party electronic device such as a mobile phone, tablet, communications tower, or a Wi-Fi hotspot in accordance with one or more user settings. For example, the speakers 73 may communicate music communicated from a radio tower of a radio station at a reduced volume in addition to communicating or producing certain artificial noises such as noises made by heavy machinery when in use. In addition, the speakers 73 may be positioned proximate to a temporal bone of the user to conduct sound for people with limited hearing capacity. More than one speaker 73 may be operably coupled to the housing 11 and the processor 40.

The processor 40 is operably coupled to the housing 11, the microphones 18 & 20, and the speakers 73 and is programmed to characterize an environment associated with the ambient sound. The characterization of the environment by the processor 40 may be performed using the ambient sounds received by the microphones 18 & 20. For example, the processor 40 may use a program or an algorithm stored in a memory or the processor 40 itself on the ambient sound to determine or approximate the environment in which jackhammer sounds, spoken phrases such as "Don't drill too deep!" or other types of machinery sounds originate, which in this case may be a construction site or a road repair site. In addition, the processor 40 may use sensor readings or information encoded in a signal received by a third party electronic device to assist in making the characterization of the environment. For example, in the previous example, the processor may use information encoded in a signal received from a mobile device using a third-party program such as Waze® to determine the ambient sounds come from a water main break is causing a severe traffic jam. In addition, the processor 40 is programmed to modify the ambient sound based on a set of parameters associated with the environment. The modification may be performed in accordance with one or more user settings. The user settings may include, for example, to amplify the sounds of speech patterns if the sound level of the origin of the sounds is low, to attenuate the sounds of machinery if the sounds exceed a certain decibel level, to remove all echoes regardless of environment, or to filter out sounds having a profile like crowd noise when attending a live entertainment event. The set of parameters may also be based on one or more sensor readings, one or more sounds, or information encoded in a signal received by a transceiver.

The processor 40 is the logic controlling the operation and functionality of headset 10. The processor 40 may include circuitry, chips, and other digital logic. The processor 40 may also include programs, scripts, and instructions implemented to operate the processor 40. The processor 40 may represent hardware, software, firmware, or any combination thereof. In one embodiment, the processor 40 may include one or more processors, such as microprocessors. The processor 40 may also represent an application specific integrated circuit (ASIC) or field programmable gate array (FPGA).

For example, a processor included in the processor 40 is circuitry or logic enabled to control execution of a set of instructions. The processor may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, and performing other related tasks. The processor may also manage transmission and reception of audio and data, GPS information, wireless LAN, GSM, or LTE, SIM or data cards, or so forth. The processor may be a single chip or integrated with other computing or communications elements of the headset 10.

Memory 45 may be operably coupled to the housing 11 and the processor 40 and may have one or more programs, applications, or algorithms stored within may be used in characterizing an environment associated with an ambient sound or modifying the ambient sound based on a set of parameters associated with the environment utilizing environmental characterization. For example, the memory 45 may have a program which compares sound profiles of ambient sounds received by the microphones 18 & 20 with one or more sound profiles of certain types of environments. If the sound profile of an ambient sound substantially matches one of the sound profiles in the memory 45 when the program is executed by the processor 40, then the processor 40 may determine an environment is successfully characterized with the ambient sound. In addition, the memory 45 may have one or more programs or algorithms to modify the ambient sound in accordance with a set of parameters associated with the environment. For example, if the user desires the converse with someone while wearing a headset 10, then the processor 40 may execute a program or application stored on the memory 45 to attenuate or eliminate all ambient sounds not substantially matching a sound profile like the sound of a human voice. The memory 45 may also have other programs, applications, or algorithms stored within not related to characterizing an environment or modifying an ambient sound.

The memory 45 is a hardware component, device, or recording media configured to store data for subsequent retrieval or access later. The memory 45 may be static or dynamic memory. The memory 45 may include a hard disk, random access memory, cache, removable media drive, mass storage, or configuration suitable as storage for data, instructions and information. In one embodiment, the memory 45 and the processor 40 may be integrated. The memory 45 may use any type of volatile or non-volatile storage techniques and mediums. The memory 45 may store information related to the status of a user and other peripherals, such as a mobile phone and so forth. In one embodiment, the memory 45 may display instructions or programs for controlling the gesture control interface 36 including one or more LEDs or other light emitting components 82, speakers 73, tactile generators (e.g., vibrator) and so forth. The memory 45 may also store the user input information associated with each command. The memory 45 may also store default, historical or user specified information regarding settings, configuration or performance of the headset 10 (and components thereof) based on the user contact with contacts sensor(s) 38 and/or gesture control interface 36.

The memory 45 may store settings and profiles associated with users, speaker settings (e.g., position, orientation, amplitude, frequency responses, etc.) and other information and data may be utilized to operate the headset 10. The headset 10 may also utilize biometric information to identify the user so settings and profiles may be associated with the user. In one embodiment, the memory 45 may include a database of applicable information and settings. In one embodiment, applicable gesture information received from the gesture interface 36 may be looked up from the memory 45 to automatically implement associated settings and profiles.

One or more sensors 38 may be operably coupled to the housing 11 and the processor 40 and may be positioned or configured to sense various external stimuli used to better characterize an environment. One or more sensors 38 may include a chemical sensor 79, a camera 300 or a bone conduction sensor 71. For example, if the microphones 18 & 20 pickup ambient sounds consisting of a blazing fire but a chemical sensor 79 does not sense any smoke, this information may be used by the processor 40 to determine the user is not actually near a blazing fire, but may be in a room watching a television program currently showing a blazing fire. In addition, an image or video captured by a camera 300 may be employed to better ascertain an environment associated with an ambient sound. A bone conduction sensor 71 may also be used to ascertain whether a sound originates from the environment or the user. For example, to differentiate whether a voice originates from a third party or the user, a timing difference between when the voice reaches the microphones 18 & 20 and when the voice reaches the bone conduction sensor 71 may be used by the processor 40 to determine the origin of the voice. Other types of sensors may be employed to improve the capabilities of the processor 40 in characterizing an environment associated with one or more ambient sounds.

Transceiver 46 may be disposed within the housing 11 and operably coupled to the processor 40 and may receive signals from or transmit signals to another electronic device. The signals received by the transceiver 46 may encode data or information related to a current environment or parameters associated with the environment. For example, the transceiver 46 may receive a signal encoding information regarding the user's current location, which may be used by the processor 40 in better characterizing an environment. The information may come from a mobile device, a tablet, a communications tower such as a radio tower, a Wi-Fi hotspot, or another type of electronic device. In addition, the transceiver 46 may receive signals encoding information concerning how the user wants an ambient sound modified. For example, a user may use a program on a mobile device such as a smartphone to instruct the headset 10 to attenuate a loud uncle's voice if the microphones 18 & 20 receives such a sound and transmit the instructions to the memory 45 or processor 40 of the headset 10 using the smartphone, which may be received by the transceiver 46 before being received by the processor 40 or memory 45. The transceiver 46 may also receive signals encoding data related to media or information concerning news, current events, or entertainment, information related to the health of a user or a third party, information regarding the location of a user or third party, or information concerning the functioning of the headset 10. More than one signal may be received from or transmitted by the transceiver 46.

The transceiver 46 may receive or transmit more than one signal simultaneously. For example, a transceiver 46 in a right ear portion 16 may transmit a signal encoding instruction for modifying a certain ambient sound (e.g. thunder) to a left ear portion 14 while receiving a signal encoding instruction for modifying crowd noise from the left ear portion 14. The transceiver 46 may be of any number of types including a near field magnetic induction (NFMI) transceiver.

Gesture interface 36 may be operably coupled to the housing 11 and the processor 40 and may be configured to allow a user to control one or more functions of the headset 10. The gesture interface 36 may include at least one emitter 82 and at least one detector 84 to detect gestures from either the user, a third party, an instrument, or a combination of the aforementioned and communicate one or more signals representing the gesture to the processor 40. The gestures may be used with the gesture interface 36 to control the headset 10 including, without limitation, touching, tapping, swiping, use of an instrument, or any combination of the gestures. Touching gestures used to control the headset 10 may be of any duration and may include the touching of areas not part of the gesture interface 36. Tapping gestures used to control the headset 10 may include any number of taps and need not be brief. Swiping gestures used to control the headset 10 may include a single swipe, a swipe changes direction at least once, a swipe with a time delay, a plurality of swipes, or any combination of the aforementioned. An instrument used to control the headset 10 may be electronic, biochemical or mechanical, and may interface with the gesture interface 36 either physically or electromagnetically.

LEDs 30s may be operably coupled to the housing 11 and the processor 40 and may be configured to provide information concerning the headset 10. For example, the processor 40 may communicate a signal encoding information related to the current time, the battery life of the headset 10, the status of another operation of the headset 10, or another earpiece function to the LEDs 302, which may subsequently decode and display the information encoded in the signals. For example, the processor 40 may communicate a signal encoding the status of the energy level of the earpiece, wherein the energy level may be decoded by LEDs 302 as a blinking light, wherein a green light may represent a substantial level of battery life, a yellow light may represent an intermediate level of battery life, a red light may represent a limited amount of battery life, and a blinking red light may represent a critical level of battery life requiring immediate recharging. In addition, the battery life may be represented by the LEDs 302 as a percentage of battery life remaining or may be represented by an energy bar having one or more LEDs, wherein the number of illuminated LEDs represents the amount of battery life remaining in the earpiece. The LEDs 302 may be in any area on the headset 10 suitable for viewing by the user or a third party and may also consist of as few as one diode which may be provided in combination with a light guide. In addition, the LEDs 302 need not have a minimum luminescence.

Battery 47 is operably coupled to all the components within the headset 10. The battery 47 may provide enough power to operate the headset 10 for a reasonable duration of time. The battery 47 may be of any type suitable for powering headset 10. However, battery 47 need not be present in the headset 10. Alternative battery-less power sources, such as sensors configured to receive energy from radio waves (all of which are operably coupled to one or more headset 10) may be used to power the headset 10 in lieu of a battery 47.

Figure 4:
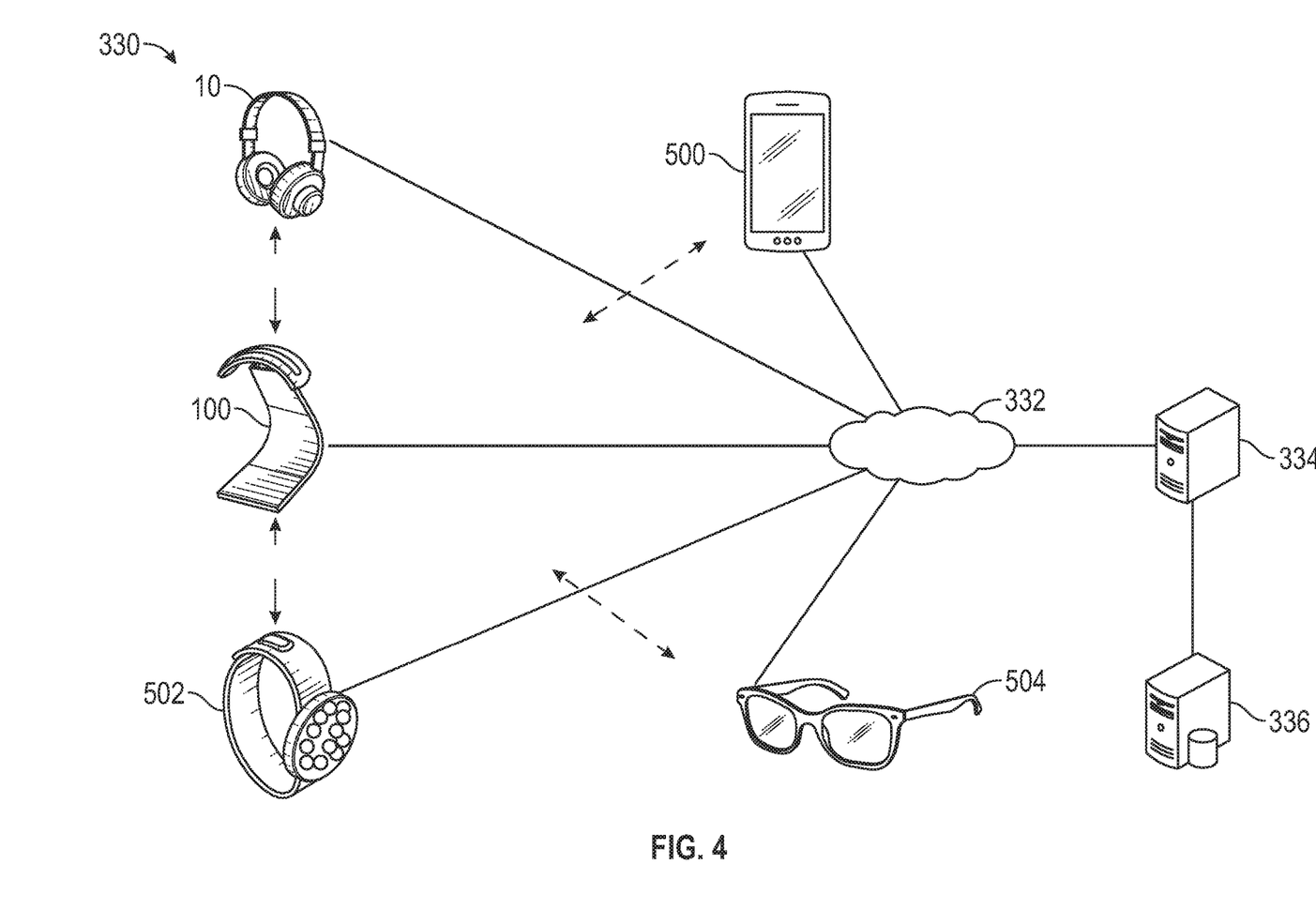
FIG. 4 illustrates a communication system in accordance with embodiments of the present invention.

FIG. 4 illustrates another embodiment of a headset system 330 including a headset charger 100, headset 10, a mobile phone 500, a smart/biometric watch 502, smart/biometric eyewear 504, a network 332, a server platform 334 and a database server 336. Communication requests submitted via the headset 10 may be transmitted to a network 300, which may subsequently retransmit the communication request to one or more headset charger 100, mobile phone 500, watch 502, eyewear 504 or a server platform 334 or the communication requests may be sent directly as shown by the broken arrows of FIG. 4. Transmissions other than communication requests may also be transmitted to the network 332 and subsequently transmitted to headset 10, mobile phone 500, bracelet 502, eyewear 504 or the server platform 334. If mobile phone 500, watch 502, eyewear 504 or headsets 12 are within range for direct communications, then headset charger 10 can communicate directly with each device without the need for network 332.

In addition, requests or other transmissions may also be communicated or transmitted by another/secondary user to the network 332 using headset 10, mobile phone 500, watch 502 or eyewear 504. Communications and transmissions received by the server platform 334 may be further transmitted to a database server 336 to be analyzed, processed or stored for future use. For example, communications or transmissions encoding user information, financial information or biometric information received by the server platform 334 may be compared to information in the database server 336 to verify identity before communicating or transmitting a request or a reply to the user or an alternate user.

In addition, information encoded in communications or transmissions received by the server platform 334 may be compared to data or information in the database server 336 to assist in verifying or authenticating the identity of users, provide location-dependent services to the user or users, develop a detailed profile of the user or assist advertisers in targeting advertisements to the user or users. Assistance with operating the headset 10 may also be communicated to the headset 10 or the headset charger 100 if it is determined by the server platform 334 the user is having difficulty using the headset 10 or the headset charger 100 or if one or more functionalities of the headset 10 or headset charger 100 is not operating within normal parameters. In addition, media such as music, fitness programs, news or weather reports, podcasts or advertisements may be stored in the server platform 334 or database server 336 and communicated to the user's headset 10 or headset charger 100 if desired.

Figure 5:
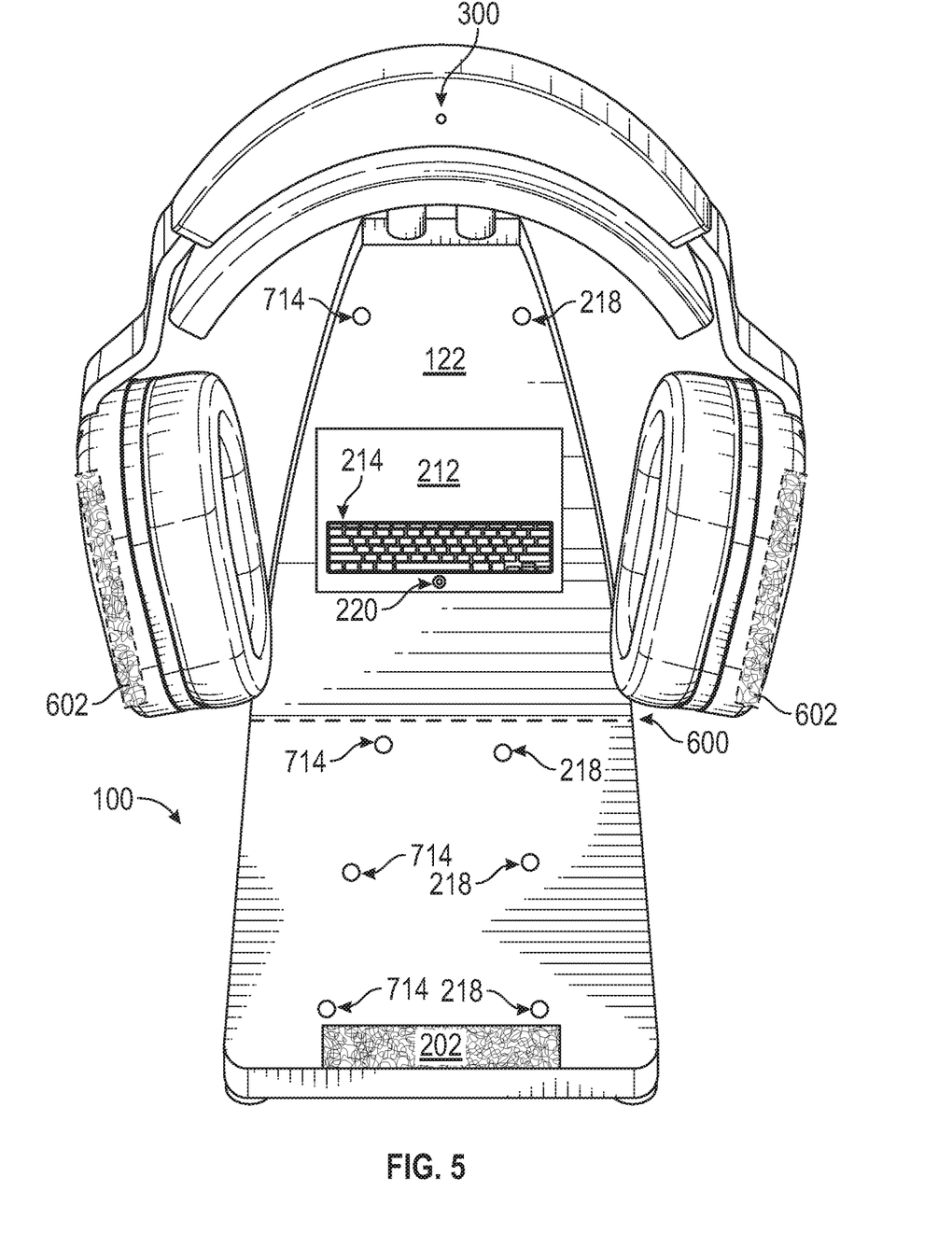
FIG. 5 shows a pictorial representation of a headset charger and headsets in accordance with an illustrative embodiment.

With reference to FIG. 5, a pictorial representation of a headset charger and headset in accordance with an illustrative embodiment is shown. In the embodiment of FIG. 5, headset charger 100 has a plurality of microphones 218 spread out over headset charger 100. Microphone(s) 218 could be located all over headset charger 100 (i.e., also on the sides and back not shown in FIG. 5) to provide intake of audio and provide directional identification of an audio source. Microphone(s) 218 can also provide authentication for interactions and transactions requiring or desiring additional verification and/or security. The headset 10 could support smart assistants/artificial intelligence systems, such as Siri®, Cortana®, Alexa®, Google®, Watson®, or other smart assistants/artificial intelligence where purchases can be made over network 332. It is contemplated a user could order on Amazon® from headset 10 through voice (i.e., the microphone(s) 18 & 20) with authentication to purchase provided by voice recognition. It is contemplated a user could be at a location remote from the headset charger 100 and utilizing the headset 10 connect with the headset charger 100 to have a conversation with his(er) family while they are at home utilizing speaker 202. The user could also communicate with his(er) office or office assistant in a similar fashion.

As stated above, microphone(s) 18, 20 & 218 could be used to perform voice recognition for a user based upon a voice-fingerprint stored in the memory 45. Two or more of these security features could provide a robust authentication feature to the headset 10. So, for example, the user decides to purchase something from Amazon® through Alexa®. The user would say, "Alexa, please order me a new pair of CrossFit® training shoes." Headset 10 would begin the ordering process including pulling the users purchasing information (e.g., credit and/or debit card information) from memory 45 and then request a voice authentication. The user would speak and headset 10 would verify the voice captured by microphone(s) 18, 20 & 218 with a voice recorded in memory 45. After this first authentication was finished, headset 10 could then ask for the user to place his face in front of camera 300. The camera 300 could record the user's face and compare it to a stored photo of the user for facial recognition and the purchase would be executed and or halted depending on the results of the facial recognition authentication.

One or more microphone(s) 218, in addition to being operatively coupled to the headset charger 100, may also be configured to sense one or more sounds. The sounds may originate from the user, a third party, a machine, an animal, headset 10, another electronic device, or even nature itself. The types of sounds received by the microphones 218 may include words, combinations of words, sounds, combinations of sounds, or any combination of the aforementioned. The sounds may be of any frequency and need not necessarily be audible to the user. Microphone 218 could be most any type of microphone 218 without departing from the spirit of the invention. Microphone 218 could be a large diaphragm condenser, a small diaphragm condenser, a dynamic, a bass, a ribbon, a multi-pattern, a USB or a boundary microphone or any combination of these microphones listed in embodiments of the present invention.

Headset charger 100 can have a speaker 202 for producing audio output. The speaker 202, in addition to being operatively coupled to the headset charger 100, may also be configured to produce one or more sounds. The sounds may be communicated to a user of the headset 10. The speaker 202 may also produce sounds received from other inputs. For example, the speaker 202 may produce audio signals received from a radio transceiver along with any sounds the user desires to hear. The sounds could be music stored in memory 45. Also, the speaker 202 may short out if either an audio signal or an ambient sound is too loud or exceeds a certain decibel threshold, which may be programmable by the user. Speaker 202 could be most any type of speaker 202 without departing from the spirit of the invention. Speaker 202 could be full-range drivers, a subwoofer, a woofer, a mid-range driver, a tweeter, a coaxial driver or a horn loudspeaker or any combination of these speakers listed above. Speaker 202 can have loudspeaker functionality as well.

Headset charger 100 can have a camera 220 located just below interactive display 212. Camera 220 can be used for tele-conferencing, watching video and security aspects such as facial recognition and fingerprint recognition. For example, a user can place her finger over the camera 220 to enable the headset charger 100 to detect her fingerprint. The fingerprint could then be compared with those stored in memory 45 to determine whether the user can have access to headset 10. Camera 220 can be most any type of camera 220, such as an analog or digital camera. It could be most any type of camera currently implemented in a mobile phone or other computing device now or in the future.

The display 212 of the headset charger 100 may display one or more headset users, device identifier, nicknames or other identifiers the headset charger 100 is currently coupled to, communicated with in the past or may wish to connect with. The display 212 may also display other media or functions coupled with the processor 204 or may display media or functions related to other applications. The user can view interactive display 212 in a T.V. or theater fashion.

A user interface 214 can be executed in a virtual fashion on display 212 (e.g., a virtual keyboard) and can be used to select a mode of operation, such as headset charger operation, theater mode or communications mode. It could be used to set variables of the headset charger 100, such as volume, base, treble, brightness, contrast, etc. It could be used to pick a functionality, such as playing music stored in memory 45, picking a terrestrial radio station, playing YouTube® videos, an IHeart Radio® station, ordering online from Alexa®, playing videos stored in memory, watching digital TV, locating and connecting to WIFI hotspots and mobile devices (headset charger 100 could be electronically and/or wirelessly coupled to most any electrical device capable of communicating). When not in use, user interface 214 would disappear thus providing more of display 212 to present whatever materials the user may be viewing. It is contemplated a stylus could be used with user interface 214 as presenting a virtual keyboard on a small screen can be difficult to use for those with large hands.

Headset charger 100 has a plurality of environmental sensors 714. Environmental sensors 714 can provide valuable information to a user. Information such as ambient temperature, air pressure, lumens measurement, humidity, etc. This information can be used in a variety of fashions. For example, if the user is outside using headset charger 100 and environmental sensors 714 detect a drop in lumens (e.g., sunlight) mixed with air pressure and temp falling, headset charger 10 could examine the local weather and verify there is a chance for rain. If the verification is correct, a message could appear on display 212 and/or broadcast over speaker 202 notifying the user they may want to put headset charger 100 away or move inside as there is rain on the way.

Through headset charger system 330, headset 10 could keep track of a user's sleep and sport activities by obtaining information from headset 10 and watch 502, both of which have biometric recording capabilities. Further, watch 502 could be worn during sleep so headset 10 could examine a user's sleep patterns and advise the user through display 212 and/or speaker 202 of how the user is sleeping and advise the user how to get better sleep through instructional videos.

It is further contemplated headset charger 100 could rotate along axis 600. Thus, a user could rotate extension platform 122 towards and away from the user. This would help if the user was using camera 220 and the user needed to adjust the camera angle. And, this could assist the user in properly viewing the display 212, e.g., to reduce glare or put the display 212 into proper line-of-sight for proper viewing based on the height of the user. It is further envisioned, headset 10 could have outer speakers 602. Outer speakers 602 could lie on the outside of left earpiece 14 and right earpiece 16. Thus, there would be speakers on the interior of headset 10 for use when a user is wearing headset 10 (i.e., in the traditional wearing of headsets); however, when headset 10 are docked on headset charger 100, outer speakers 602 and the inner speakers as well as speaker 202 could be used to provide enhanced audio, even surround sound and/or 3-D audio.

Therefore, various methods, apparatus, and systems associated with an intelligent wireless headset have been shown and described. The present invention is not to be limited to the specific embodiments shown herein but to the inventive aspects which are claimed. Numerous options, variations, and alternatives are contemplated including variations in the style and shape of the headset, the selection, number, and placement of sensors, the functionality provided and other options, variations, and alternatives.

What is claimed is:

1. An intelligent wireless headset, comprising:
a left ear portion having at least one microphone and at least one speaker associated therewith;
a right ear portion having at least one microphone and at least one speaker associated therewith;
a connecting band between the left ear portion and the right ear portion;
at least one sensor operably coupled to the left or the right ear portion;
a left ear cushion on an interior portion of the left ear portion;
a right ear cushion on an interior portion of the right ear portion;
a left hard exterior surface at an exterior portion of the left ear portion;
a right hard exterior surface at an exterior portion of the right ear portion;
a gestural interface disposed within the left or the right ear portion wherein the gestural interface receives gestures from a user at the left hard exterior surface or the right hard exterior surface using optical detectors;
a processor disposed within the intelligent wireless headset and operatively connected to the at least one microphone of the left ear portion, the at least one speaker of the left ear portion, the at least one microphone of the right ear portion, the at least one speaker of the right ear portion, and the at least one sensor on the left or the right ear portion; wherein the processor is configured to receive various external stimuli from the at least one sensor and process the ambient sound from the left ear portion and the ambient sound from the right ear portion and reproduce a processed version of the ambient sound from the left ear portion at the at least one speaker of the left ear portion and a processed version of the ambient sound from the right ear portion at the at least one speaker of the right ear portion based on the various external stimuli characterizing the ambient environment;
a wireless radio transceiver disposed within the intelligent wireless headset; and
a cellular transceiver disposed within the intelligent wireless headset.

2. The intelligent wireless headset of claim 1 wherein a first of the at least one microphone of the left ear portion is positioned to detect ambient sound.

3. The intelligent wireless headset of claim 2 wherein a first of the at least one microphone of the right ear portion is positioned to detect ambient sound.

4. The intelligent wireless headset of claim 1 further comprising at least one imaging sensor mounted on the right ear portion.

5. The intelligent wireless headset of claim 4 further comprising at least one imaging sensor mounted on the left ear portion.

6. The intelligent wireless headset of claim 4 wherein the at least one imaging sensor is a time of flight sensor.

7. The intelligent wireless headset of claim 1 further comprising a plurality of microphones arranged along the connecting band.

8. The intelligent wireless headset of claim 7 wherein the plurality of microphones are arranged along the connecting band in a beamforming array.

* * * * *